United States Patent [19]

Bormann et al.

[11] 3,957,771

[45] May 18, 1976

[54] PROCESS FOR THE MANUFACTURE OF AMINOAZETIDINONES

[75] Inventors: Dieter Bormann, Kelkheim, Taunus; Manfred Schorr, Frankfurt am Main; Wilfried Schmitt, Kelkheim, Taunus, all of Germany

[73] Assignee: Hoechst Aktiengesellschaft, Frankfurt am Main, Germany

[22] Filed: May 3, 1973

[21] Appl. No.: 356,933

[30] Foreign Application Priority Data

May 5, 1972  Germany............................ 2222094

[52] U.S. Cl..................... 260/243 R; 260/306.7 C; 260/243 C
[51] Int. Cl.$^2$................ C07D 279/08; C07D 277/60
[58] Field of Search......... 260/243 R, 306.7, 243 C, 260/306.7 R

[56] References Cited

UNITED STATES PATENTS

| | | |
|---|---|---|
| 3,499,909 | 3/1970 | Weissenburger et al. ........ 260/306.7 |
| 3,575,970 | 4/1971 | Weissenburger et al. .......... 260/243 |
| 3,676,429 | 7/1972 | Weissenburger et al. ... 260/306.7 X |
| 3,875,151 | 4/1975 | Fechtig et al. .................. 260/243 R |

*Primary Examiner*—John M. Ford
*Attorney, Agent, or Firm*—Curtis, Morris & Safford

[57] ABSTRACT

The present invention relates to a new process for the preparation of 6-aminopenicillanic acid and 7-amino-cephalosporanic acid derivatives by treating the corresponding acylamino derivatives with phosphinic acid chlorides, reacting the mixed acid anhydrides so obtained with agents forming imidohalides, converting the imido halides into iminoethers and hydrolysing them.

5 Claims, No Drawings

PROCESS FOR THE MANUFACTURE OF AMINOAZETIDINONES

The present invention relates to a process for the manufacture of aminoazetidinones.

These aminoazetidinones have the general formula I

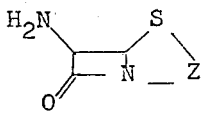   I wherein Z is defined as follows:

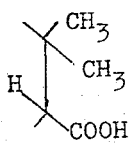   or   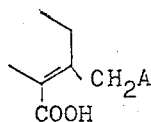

wherein A is hydrogen, acyloxy, alkyloxy or hydroxy.

The novel process comprises reacting acylamino derivatives of the general formula II

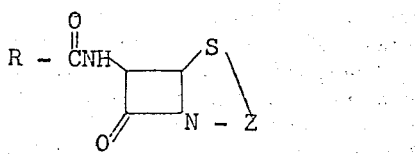   II wherein Z is defined as above and R is hydrogen or an optionally substituted alkyl, aryl, aralkyl, aryloxyalkyl, alkoxyalkyl or heterocyclic radical, in the form of their salts with phosphinic acid chlorides of the general formula III,

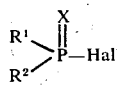   III wherein the radicals $R^1$ and $R^2$ each are identical or different alkyl or aryl radicals, X is an oxygen atom or a sulphur atom and Hal is a halogen atom, preferably chlorine, and reacting the mixed acid anhydrides so obtained with agents forming imidohalides under waterfree conditions, converting the imidohalides so obtained into iminoethers, hydrolysing them with water and precipitating them by raising the pH to reach the range of the isoelectric point.

It is known that acylamino derivatives can be split into amines and carboxylic esters according to the following scheme (formation of imidochloride: Chem. Ber. 28, 2367 (1895); formation of iminoether: J. Chem. Soc. 83, 321 (1903); splitting of imino ether: Houben-Weyl 8, 700 (1952).

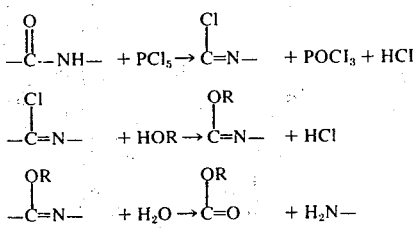

This reaction can be applied to acyl derivatives of the aminoazetidinones of the formula II under the condition that no further groups in the molecule can be reacted with reactants forming imidohalides, so that in substances having the formula II the reactive groups contained therein must be protected. This especially applies to the carboxyl group.

These groups can be protected according to different methods. The acid group, for example, can be esterified with various reactants. In these cases, the ester group must be split after the acyl group has been split by various, partially complicated chemical operations in order to regenerate the free carboxyl group [cf. Helv. Chim. Acta 51, 1108 (1968), German Offenlegungsschrift No. 1 770 712].

The introduction of the silyl esters was a step forward [cf. Liebigs Ann. Chem. 673, 166 (1964)]. These esters are rapidly split when adding water but they permit reaction of the acylamino group of compounds of the general formula II with agents forming imidohalides (cf. U.S. Pat. Nos. 3,499,909; 3,575,970; and 3,676,429).

These esters have, however, the considerable drawback that the reaction with agents forming imidohalides and the reaction of the imidohalides so obtained with alcohol to form the imino ethers must be carried out at temperatures at which the manufacture of the corresponding aminoazetidinone carboxylic acids on an industrial scale is difficult and expensive. The upper limit of the reaction temperature is indicated to be −10°C. To obtain high yields it is required to carry out the reaction at −30° to −50°C [cf. Recueil 89, 1081 (1970)].

In contradistinction thereto, it was, now, surprisingly found that phosphorus compounds of the general formula III react with salts of carboxylic acids which are derived from the general formula II to yield mixed anhydrides the acylamino substituents of which can be converted with agents forming imidohalides into imidohalides already at temperatures above −10°C. Then, the imidohalides can be converted into iminoethers in known manner at the same temperature and can be split by hydrolysis. But at the same time, the phosphinic acid radical introduced as a protective group is eliminated so that by raising the pH into the range of the isoelectric point the aminoazetidinones of the formula I precipitate in the form of extremely pure crystals.

In the compounds used as starting materials R can be hydrogen, an optionally substituted alkyl radical, especially one having from 1 to 8 carbon atoms, preferably from 1 to 5, the substituents preferably used being an amino or carboxyl group. As optionally substituted aryl radical there may especially be mentioned phenyl, which may, for example, be substituted by halogen, preferably, by chlorine or bromine low molecular weight alkoxy, preferably methoxy, or hydroxy. If R is an aralkyl radical, there may especially be mentioned the benzyl radical which may be substituted in the aromatic ring, for example, by halogen, preferably chlorine, low-molecular weight alkoxy, or hydroxy, and in the alkyl part, for example, by low-molecular weight alkyl, preferably , methyl, ethyl, and propyl, by the amino group, halogen, preferably chlorine, an azide group, low-molecular weight alkoxy, preferably methoxy, and low-molecular weight acyloxy, preferably acetoxy. If R is defined as an aryloxyalkyl group, there may especially be considered a phenyloxyalkyl radical, in which case the alkyl part may be an optionally branched low-molecular weight alkyl group having, preferably, from 1 to 5 carbon atoms and the side-chains possibly present may, preferably, have from 1 to 2 carbon atoms. The aromatic part may, for example, be substituted by halogen, preferably, chlorine, low-molecular weight alkoxy or hydroxy.

The alkyloxyalkyl radical used is, preferably a low-molecular weight radical. When using a compound of formula II having a heterocyclic radical R, it can be linked to the carbonyl group either directly or by means of a low-molecular weight alkyl or oxyalkyl group, preferably a methyl or oxymethyl group. There may, for example, be used a thienyloxymethyl, a thienylmethyl, a pyridylmethyl or an isoxalyl group.

If A stands for acyloxy, there may especially be mentioned low-molecular weight aliphatic acyloxy having from 1 to 5 carbon atoms, such as, for example, acetoxy, propionyloxy, butyryloxy, and valeryloxy; if A stands for alkyloxy, there may especially be mentioned low-molecular weight alkyloxy having from 1 to 5 carbon atoms, for example, methoxy, ethoxy, butoxy, and pentoxy.

The salts of carboxylic acids which are derived from the compounds of the general formula II are the salts of the penicillins and cephalosporins.

The manufacture of these compounds is the object of various patents. The acyl group is advantageously split from salts which are prepared on an industrial scale by means of biological methods.

There may expecially be mentioned penicillin G and penicillin V which are obtained as the sodium or potassium salt or as a salt of organic bases. A summary of the biochemical processes can be found in R. Brunner and G. Machek: "Die Antiobiotika", published by Hans Carl, volume 1, page 149 et seq. (1962).

However, other semi-synthetic penicillins, for example, propicillin, pheneticillin, methicillin, oxacillin, and cloxacillin may be split according to the process of the invention.

The cephalosporins to be considered are, especially cephalosporin C and the salts of desacetoxycephalosporanic acids.

The salts of compounds of the general formula II which can be used are of the most various kind, especially, however, those which are obtained in the biological or chemical processes for the preparation of penicillins and cephalosporins mentioned above, for example, alkali metal, alkaline earth metal or ammonium salts, in which case "ammonium" stands in a wide range for nitrogen containing cations of the type

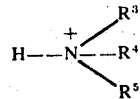

wherein the radicals $R^3$, $R^4$ and $R^5$ are identical or different low molecular weight alkyl groups and $R^3$ and $R^4$ may be linked to form a cycle. But "ammonium" shall also stand for cations containing nitrogen in which nitrogen is part of an aromatic ring system, for example in pyridine or quinoline, or for those in which alkyl and aryl groups are together linked to nitrogen, for example, in the case of the N,N-dimethyl-anilinium salt.

In the phosphinic acid halides of the formula III

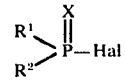

III necessary to protect the carboxylic acid function, $R^1$ and $R^2$ may be identical or different and may represent a linear or branched alkyl group, preferably having from 1 to 10 carbon atoms, especially from 1 to 8, a cycloalkyl group, preferably having from 5 to 7 carbon atoms or aryl, preferably phenyl. To carry out the reaction according to the invention, the halides preferably used are the chlorides.

The phosphinic acid halides which can be used for the process of the invention are, for example: dimethylphosphinic acid chloride, methylethylphosphinic acid chloride, methylhexylphosphinic acid chloride, methyloctylphosphinic acid chloride, dioctylphosphinic acid chloride, methyldecylphosphinic acid chloride, methylphenylphosphinic acid chloride, diphenylphosphinic acid chloride, dicyclohexylphosphinic acid chloride, dicyclopentylphosphinic acid chloride or dipropylphosphinic acid chloride. The corresponding thiophosphinic acid chlorides may also be used.

The compounds of formula III are obtainable by different methods. A clear summary of the preparation methods and of the various compounds can be found in Houben-Weyl 12/1, pages 240 to 247 (1963). Dimethylphosphinic acid chloride, for example, is obtained by oxidation of dimethylphosphine chloride or by the reaction of dimethylphosphinic acid with phosphorus pentachloride in dry benzene.

The reaction in which the anhydride is formed is effected in a dry, inert solvent.

Inert solvents are, for example, chlorinated hydrocarbons, such as methylene chloride, chloroform or ethylene chloride, but also ethers, for example, tetrahydrofurane or dioxane, or esters, for example ethylacetate.

The reaction occurs in a wide temperature range; in some cases it is necessary to heat, in other cases the temperature should not exceed +30°C.

A most advantageous embodiment of the process of the invention is to associate the components at about 0° to +10°C. in methylene chloride, and in many cases it is especially advantageous to add an equimolar amount, preferably an about 2 to 3-fold excess amount of tertiary amine. A suitable tertiary amine is, for example, N,N-dimethylaniline, pyridine, or triethyl amine.

The mixed anhydride is reacted with agents forming imidohalide without isolation, the hydrohalogen set free in the reaction being neutralized by the above-mentioned base added.

To obtain high yields the base is suitably added to the reaction mixture before the addition of substances forming imidohalide. Especially suitable bases are trialkyl amines, for example, triethyl amine, dimethylbenzyl amine, ethyldicyclohexyl amine, but also dialkylaryl amines, for example the N,N-dimethylaniline already mentioned.

As agents forming imidohalides, acid halides may be used, for example, phosphoroxy chloride, phosphorus pentachloride, phosphorus trichloride, thionyl chloride, phosgene or oxalyl chloride. Because they are economical, thionyl chloride or phosphorus pentachloride are recommended for use.

The acylamino group is converted into the imidohalide group in an inert solvent. To simplify this operation, it is suitable to use the same solvents as in the preparation of the mixed anhydride and to introduce the agent forming imidohalides in substance or in solution.

The reaction is carried out at a temperature within the range of from about +20° to −60°C, preferably, however, of from about +10° to −10°C. The reaction can be carried out with great success already at 0°C.

The conversion of the imidohalide into an iminoether is a reaction known per se. It is effected by adding alcohols to the reaction mixture. An excess of from 5 to 40 mols of alcohol per mol of imidohalide is used for this purpose. Especially suitable are the inexpensive lower alcohols, for example, methanol, ethanol, isopropanol or butanol, to which a trace of a tertiary amine, for example dimethyl aniline, is added.

To avoid undesired side-reactions the process of the invention must be carried out with the most anhydrous alcohols possible, but the reaction itself can be effected at temperatures within the range of from −50° to +20°C, preferably of from −10° to +10°C. Using that temperature, the reaction is generally completed within 15 to 30 minutes.

The following hydrolysis of the iminoethers with water is already known in the literature In this reaction, the mixed anhydride is split and the carboxyl group is set free.

The amino acids obtained can very easily be isolated by increasing the pH of the reaction mixture with the addition of bases until the range of the isoelectric point of the amino acids obtained is reached. The amino acids precipitate in the form of very pure crystals. They are then collected by usual laboratory methods, for example, by filtration and centrifuging.

The aminoazetidinone-carboxylic acids of the formula I so manufactured are valuable intermediates for the manufacture of antibiotically active substances which can be manufactured according to the invention in a surprisingly simple reaction series at a temperature range which can easily be maintained when working on an industrial scale which is particularly money-saving.

Although far-reaching research has already been made into the reactions of phosphinic acid halides, especially of the chlorides, [cf. Houben-Weyl XII, part 1, (1963), page 243], a reaction with carboxylic acids has not been known until now. It was, therefore, surprising and could not be expected that the reaction of the invention would occur.

The following Examples illustrate the invention. In all these Examples usual laboratory measures provided that the reaction was carried out with the exclusion of moisture. The solvents used were rendered absolute in known manner.

Example 1

To a suspension of 15.52 g (= 40 mmols) of penicillin-V-potassium in 60 ml of absolute methylene chloride, 10 ml of N,N-dimethylaniline and 5.06 g (= 40 mmols) of methylethylphosphinic acid chloride were successively added dropwise, at 0°C, while stirring. After an hour at 0°C the solution was cooled to −5°C and within 5 minutes 9.0 g (= 43 mmols) of phosphorus pentachloride were introduced portionwise.

The reaction mixture was stirred for 30 minutes at −5°C and 60 ml of n-butanol and 2 ml of dimethylaniline were then added so that the temperature was maintained at −5°C.

After another 30 minutes the reaction mixture was poured into 60 ml of ice water. With solid $NH_4HCO_3$ the pH was adjusted at 4.0 and maintained. When stirring the suspension at 0°C, 6-aminopenicillanic acid separated after some time. To complete the separation, the reaction mixture was allowed to stand for 15 hours at 0°C. After suction-filtering, washing with ice water, acetone and ether 6.63 g (=79 % of the theory) of 6-aminopenicillanic acid were obtained in the form of colorless crystals having a melting point of 195°C (decomposition), which is identical with authentic with authentic 6-aminopenicillanic acid according to the IR-spectrum and the mixed melting point.

Example 2

To a suspension of 14.9 g of penicillin-G-potassium in 60 ml of absolute methylene chloride, 5.06 g (=40 mmols) of methylethylphosphinic acid chloride and 10 ml of dimethylaniline were added in the same manner as indicated in Example 1. **The mixture was stirred for 1 hour and the solution of the mixed anhydride so prepared was converted at −5°C with 9.0 g (= 43 mmols) of phosphorus of pentachloride into the imidochloride. After addition of 60 ml of n-butanol and 2 ml of N,N-dimethylaniline, the mixture was stirred at −5°C for 30 minutes. 60 ml of ice water were added and the 6-aminopenicillanic acid was separated at pH 4. 6.47 g (= 76.4 % of the theory) of 6-aminopenicillanic acid were isolated in the form of colorless crystals having a melting point of 195°C (decomposition) which are identical with authentic 6-aminopenicillanic acid according to the IR-spectrum and the mixed melting point.

Example 3

When proceeding in the same manner as described in Example 1 6.54 g (32 77.3 % of the theory) of 6-aminopenicillanic acid were obtained from 14.25 g of penicillin-G-sodium after converting it into the mixed anhydride with methylethylphosphinic acid chloride by reacting with phosphorus pentachloride, n-butanol and following hydrolysis.

Example 4

To a suspension of 14.9 g of penicillin-G-potassium in 60 ml of absolute methylene chloride, 10 ml of N,N-dimethylaniline and 4.50 g (= 40 mmols) of dimethylphosphinic acid chloride were added at 0°C, while stirring. After an hour at 0°C, 9.0 g (= 43 mmols) of phosphorus pentachloride were introduced portionwise within 5 minutes. The reaction mixture was stirred again at 0°C for 30 minutes and 60 ml of n-butanol and 2 ml of N,N-dimethylaniline were added at 0°C. After 30 minutes, hydrolysis followed as described in Example 1 and 6-amoinopenicillanic acid was isolated. 5.47 g (= 63.3 %) of the said acid were obtained in the form of colorless crystals having a melting point of 195°C (decomposition), the identity of which was examined as described in Example 1.

Example 5

To a suspension of 14.9 g of penicillin-G-potassium (= 40 mmols) in 60 ml of absolute methylene chloride 10 ml of N,N-dimethylaniline and 8.42 g (= 40 mmols) of methyl-n-octylphosphinic acid chloride were added successively while stirring. After an hour at 0°C the reaction mixture was cooled to −25°C and 9.0 g (= 43 mmols) of phosphorus pentachloride were introduced. After an hour at −25°C, 60 ml of n-butanol and 2 ml of N,N-dimethylaniline were introduced and by after-stirring for an hour at −25°C the iminoether was formed. Then, hydrolysis followed in the manner described in Example 1. 7.47 g (= 88.5 % of the theory) of 6-aminopenicillanic acid having a melting point of 195°C (decomposition) were isolated in the form of colorless crystals, the identity of which was examined in an analogous manner as described in Example 1.

Example 6

In this Example, the same reaction as effected in Example 5 was repeated at −5°C. 6.77 g (= 80 % of the theory) of 6-aminopenicillanic acid were isolated and characterized in an analogous manner as described in Example 1.

The following Table contains a list of further Examples. In all cases the mixed anhydride was formed in one hour at 0°C. The imidochloride was obtained by a 2 hours' reaction with phosphorus pentachloride at −60°C and the iminoether by a 2 hours' reaction of the imidochloride at −60°C with a mixture of 60 ml of n-butanol and 2 ml of N,N-dimethyl aniline. Hydrolysis, isolation and characterization were carried out in an analogous manner as described in Example 1.

Table

| Example No. | Penicillin | Phosphinic acid chloride | Yield |
| --- | --- | --- | --- |
| 7 | penicillin-G-potassium | $(CH_3)_2POCl$ | 71.6 % |
| 8 | " | $\begin{array}{c}CH_3\\ \phantom{xx}\diagdown\\ \phantom{xxxx}POCl\\ \phantom{xx}\diagup\\ C_2H_5\end{array}$ | 70.5 % |
| 9 | " | $\begin{array}{c}CH_3\\ \phantom{xx}\diagdown\\ \phantom{xxxx}POCl\\ \phantom{xx}\diagup\\ C_8H_7\end{array}$ | 91.0 % |
| 10 | " | $(C_6H_5)_2POCl$ | 24.3 % |
| 11 | " | $\begin{array}{c}CH_3\\ \phantom{xx}\diagdown\\ \phantom{xxxx}PSCl\\ \phantom{xx}\diagup\\ C_2H_5\end{array}$ | 17.4 % |
| 12 | penicillin-V-potassium | $(CH_3)_2POCl$ | 75.0 % |

Example 13

To a suspension of 15.78 g (= 40 mmols) of potassium salt of the 6-(thienyl-3-oxyacetamido)-2,2-dimethyl-penam-3-carboxylic acid in 60 ml of absolute methylene chloride, 4.50 g (= 40 mmols) of dimethylphosphinic acid chloride and 10 ml of N,N-dimethylaniline were added successively at 0°C and the mixture was stirred for one hour. Then the reaction mixture was cooled to −25°C and 9.0 g (= mmols) of phosphorus pentachloride were added. After an hour at −25°C, a mixture of 60 ml of n-butanol and 2 ml of N,N-dimethylaniline was added to the imidochloride so obtained, at the same temperature. After another hour hydrolysis was carried out in an analogous manner as described in Example 1, the 6-aminopenicillanic acid so obtained was isolated and characterized. 6.05 g (= 71.5 % of the theory) of 6-aminopenicillanic acid were obtained.

Example 14

To a suspension of 4.18 g (=10 mmols) of sodium salt of 7-(thienyl-2-acetamido)-cephalosporanic acid in 70 ml of dry methylene chloride, 1.27 g (=10 mmols) of methylethylphosphinic acid chloride and 2.5 ml of N,N-dimethylaniline were added at room temperature while stirring. After an hour the mixture was cooled to −10°C and 2.29 g (= 11 mmols) of phosphorus pentachloride were added. The reaction mixture was stirred at −10°C for 3 hours and then 0.5 ml of dimethylaniline and 24 ml of n-butanol were added at −10° and stirring was continued for another 2 hours. Hydrolysis was then carried out with a mixture of 30 ml of methanol and 30 ml of water, the whole was stirred again for 10 minutes at 0°C and the pH was adjusted at 7 by adding solid ammonium carbonate. After 30 minutes the pH was adjusted at 3.5 with 2 N hydrochloric acid and the reaction mixture was allowed to stand at 0°C for 15 hours.

The precipitated crystals were suction-filtered, suspended again in water and given the state of solution by adding solid sodium bicarbonate. The solution was treated with carbon powder, filtered and 7-aminocephalosporanic acid was precipitated by adding 2 N hydrochloric acid up to pH 3.5. After suctionfiltering, after-washing with ice-water, acetone, and ether, 2.25 g (= 82.5 % of the theory) of 7-aminocephalosporanic acid having a melting point of >300°C were isolated, which is identical with an authentic sample according to the IR-spectrum.

Example 15

To a suspension of 8.3 g (=20 mmols) of cephalosporin C in 100 ml of dry methylene chloride, 6.5 ml of absolute pyridine and 7.60 g (= 60 mmols) of methylethylphosphinic acid chloride were added at room temperature. After 15 minutes, 5 ml of N,N-dimethylaniline were added and the total mixture was stirred at room temperature for 1 hour.

After that time, the mixture was cooled to −5°C and to the reaction mixture 4.3 g (= 20.7 mmols) of phosphorus pentachloride were added.

After 2 hours at −5°C, a solution of 1 ml of N,N-dimethylaniline in 50 ml of absolute butanol was added, stirring was continued for another hour at the same temperature and for another 30 minutes at room temperature and the reaction mixture was poured into 50 ml of ice water. By adding solid ammonium carbonate the pH was adjusted to 3.5. After 15 hours at 0°C the precipitated crystals were isolated and purified in an analogous manner as described in Example 14.

3.57 g (= 65.5 %) of 7-aminocephalosporanic acid were obtained which had a melting point of >300°C and was identical with authentic 7-aminocephalosporanic acid according to the IR-spectrum.

Example 16

A suspension of 6.96 g (=20 mmols) of 7-phenoxyacetamido-3-desacetoxycephalosporanic acid in 80 ml of dry methylene chloride was converted with 2.02 g (= mmols) of triethylamine into the ammonium salt. The solution was cooled to 0°C, 2.25 g (= 20 mmols) of dimethylphosphinic acid chloride and 5.0 ml of N,N- dimethylaniline were added to it and after 30 minutes it was converted with 4.3 g (=20.7 mmols) of phosphorus pentachloride into the imidochloride.

After an hour at 0°C the reaction mixture was reacted with a solution of 1 ml of N,N-dimethylaniline in 30 ml of absolute methanol. After another 30 minutes the iminoether so obtained was split with 30 g of ice and 50 ml of methanol and the 7-aminodesacetoxycephalosporanic acid so obtained was isolated by adding solid ammonium bicarbonate in the manner indicated in Example 14. 2.98 g (= 69.7 % of the theory) of 7-amino-3-desacetoxy-cephalosporanic acid were otained as colorless crystals having a melting point of 246°–248°C (decomposition) and being identical with authentic 7-amino-3-desacetoxycephalosporanic acid according to the IR-spectrum and the mixed melting point.

Example 17

A suspension of 6.96 g (= 20 mmols) of 7-phenoxyacetamido-3-desacetoxycephalosporanic acid in 40 ml of dry methylene chloride was converted with 2.02 g (= 20 mmols) of triethylamine in 10 ml of methylene chloride into the ammonium salt. The solution was cooled to 10°C, 2.5 ml of N,N-dimethylaniline and 2.60 g (= 20.4 mmols) of methylethylphosphinic acid chloride were added and after 30 minutes the solution was converted into the imidochloride with a solution of 4.3 g (= 20.7 mmols) of phosphorus pentachloride in 40 ml of methylene chloride.

After 45 minutes at +10°C a solution of 1 ml of N,N-dimethylaniline and 30 ml of absolute methanol was added dropwise, the solution was stirred for 15 minutes at +10°C and for 15 minutes at room temperature and then the iminoether was hydrolysed with 30 g of ice and 50 of methanol.

After working up in an analogous manner as described in Example 14, 1.92 g (=45 % of the theory) of 7-amino-3-desacetoxycephalosporanic acid having a melting point of 247°–248°C (decomposition) were isolated.

Example 18

A suspension of 6.96 g (= 20 mmols) of 7-phenoxyacetamido-3-desacetoxycephalosporanic acid in 80 ml of dry methylene chloride was converted with 1.98 ml of piperidine (= 20 mmols) into the soluble piperidinium salt. The solution was cooled to 0°C and 4.21 g (= 20 mmols) of methyl-n-octylphosphinic acid chloride and 5 ml of N,N-dimethylaniline were added to it. After an hour at 0°C, 4.3 g (= 20.7 mmols) of phosphorus pentachloride and, after another hour at 0°C, a solution of 1 ml of N,N-dimethylaniline in 45 ml of dry n-butanol were added dropwise. The reaction mixture was poured, after another hour, into 30 ml of ice water, stirred for 10 minutes and then the pH was adjusted to 3.5 with solid ammonium bicarbonate.

After 15 hours at 0°C the crystals so obtained were suction-filtered and purified in an analogous manner as described in Example 14.

3.47 g (= 81 % of the theory) of 7-amino-3-desacetoxycephalosporanic acid having a melting point of 246°–248°C (decomposition) were obtained.

What is claimed is:

1. In a method for making an aminoazetidinone of the formula

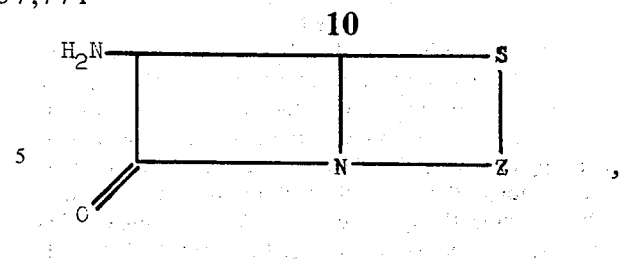

wherein Z is

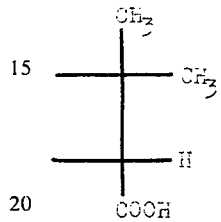 or 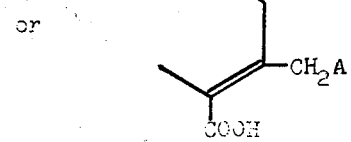

and A is hydrogen, alkanoyloxy having 1 to 5 carbon atoms, alkyloxy having 1 to 5 carbon atoms, or hydroxy, from an acylamino of the formula

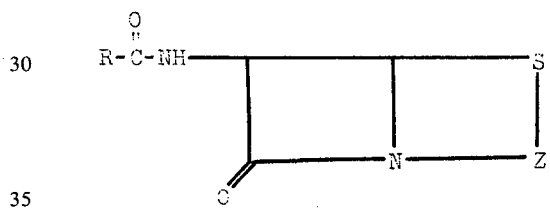

wherein the carboxy group present in Z is protected, by reacting the carboxy-protected acylamino compound under anhydrous conditions with an acid halide to form the corresponding carboxy-protected imidohalide of the formula

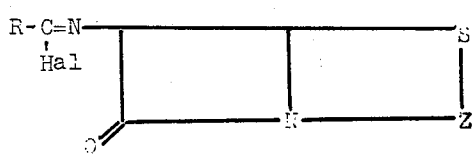

converting said carboxy-protected imidohalide into the corresponding carboxy-protected iminoether of the formula

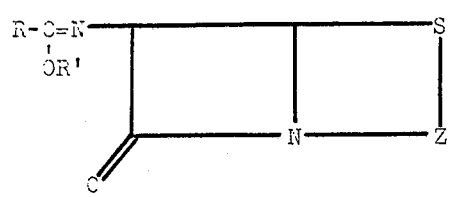

by reaction with an alcohol, hydrolyzing the carboxy-protected iminoether with water to remove the carboxy protective group and to form the desired aminoazetidinone, and then precipitating the desired aminoazetidinone by adjusting the pH of the reaction mixture into the range of the isoelectric point, the improvement wherein the carboxy-protected acylamino compound is obtained by reacting a salt of the unprotected acylamino compound, said salt being formed by neutralization of the carboxy group present in Z, with a phosphinic acid halide of the formula

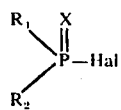

wherein $R_1$ and $R_2$ are the same or different and are alkyl having 1 to 10 carbon atoms, phenyl, or cycloalkyl having 5 to 7 carbon atoms, X is oxygen or sulfur, and Hal is halogen, to form a mixed acid anhydride between the carboxy group of Z and said phosphinic acid, which mixed acid anhydride contains the group

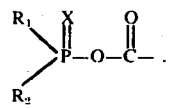

2. A method as in claim 1 wherein said phosphinic acid halide is dimethylphosphinic acid chloride, methylethylphosphinic acid chloride, methylhexylphosphinic acid chloride, methyloctylphosphinic acid chloride, or diphenylphosphinic acid chloride.

3. A method as in claim 1 wherein said reaction between said mixed anhydride and said acid halide to form an imidohalide is effected at a temperature between −10°C. and +10°C.

4. A method as in claim 1 wherein said imidohalide is reacted with an alcohol to form an iminoether at a temperature between −10°C. and +10°C.

5. A method as in claim 1 wherein said salt of said acylamino compound is formed by salification of said acylamino compound with a base immediately before reaction of said salt and said phosphinic acid.

* * * * *